United States Patent [19]

Callahan et al.

[11] 4,335,056
[45] Jun. 15, 1982

[54] PROCESSING ACRYLONITRILE WASTE GAS

[75] Inventors: James L. Callahan, Wooster; Wilfrid G. Shaw, Lyndhurst; David B. Terrill, Bedford, all of Ohio

[73] Assignee: Standard Oil Company, Cleveland, Ohio

[21] Appl. No.: 222,448

[22] Filed: Jan. 5, 1981

[51] Int. Cl.³ .............. C07C 120/14; C07C 51/215; C07C 45/35
[52] U.S. Cl. .................. 260/465.3; 562/545; 562/546; 568/476; 568/479; 568/480
[58] Field of Search ............ 260/465.3; 562/545; 568/476

[56] References Cited

U.S. PATENT DOCUMENTS

| | | | |
|---|---|---|---|
| 3,404,947 | 10/1968 | Miller et al. | 260/465.3 |
| 3,766,092 | 10/1973 | Honda et al. | 252/437 |
| 3,895,050 | 7/1975 | Sheely | 260/465.3 |
| 3,988,423 | 10/1976 | Ahrui et al. | 423/236 |
| 4,065,486 | 12/1977 | Thorpe et al. | 260/465.3 |

Primary Examiner—Dolph H. Torrence
Attorney, Agent, or Firm—John E. Miller, Jr.; Herbert D. Knudsen; Larry W. Evans

[57] ABSTRACT

In the recovery of acrylonitrile from the gross reaction product produced during the commercial ammoxidation of propylene to produce acrylonitrile, an ammoxidation waste gas containing at least 65% nitrogen, carbon dioxide, carbon monoxide and a small amount of unreacted propylene is produced. In accordance with the invention, this ammoxidation waste gas is passed through a catalytic converter containing an oxidation or ammoxidation catalyst to convert the unreacted propylene into valuable product.

5 Claims, No Drawings

PROCESSING ACRYLONITRILE WASTE GAS

BACKGROUND OF THE INVENTION

In the commercial production of acrylonitrile, propylene is ammoxidized to acrylonitrile by contacting a mixture of propylene, ammonia and oxygen with a fluid-bed catalyst. A gross reaction product is produced which contains various components in addition to acrylonitrile such as $N_2$, CO, $CO_2$, $H_2O$, unreacted propylene, hydrogen cyanide, acrolein, acetone, acetonitrile, acetaldehyde, etc.

The first step in recovering acrylonitrile from this gross reaction product is to separate the product into liquid and vaporous phases. This is accomplished by cooling the reaction product to condense higher boiling components. Cooling can be accomplished either by indirect heat exchange or by direct contact with water.

The liquid phase produced by the above procedure contains product acrylonitrile, acetonitrile, HCN and minor amounts of organic impurities. It is subjected to further processing to recover acrylonitrile, acetonitrile and HCN. The gaseous phase produced by the above technique contains roughly 85% $N_2$, 1 to 2% $O_2$, 1 to 2% propane, about 0.1 to 0.5% propylene, 3 to 6% $CO_2$, 2 to 3% CO and 3 to 5% $H_2O$.

Because of the propylene and propane in the gaseous phase, it cannot be simply discharged to the atmosphere. Rather, it is normally incinerated whereby the propylene and propane are converted to carbon monoxide and carbon dioxide. This is disadvantageous because valuable propylene is lost.

Accordingly, it is an object of the present invention to provide a new technique for processing the gaseous phase produced in the recovery of acrylonitrile from the fluid-bed ammoxidation of propylene which advantageously utilizes the propylene in the gaseous phase.

SUMMARY OF THE INVENTION

This and other objects are accomplished by the present invention in accordance with which the waste gas product produced as a byproduct in the recovery of acrylonitrile from the fluid-bed ammoxidation of propylene is passed through a catalytic converter capable of converting propylene to valuable products such as acrylonitrile, acrolein and/or acrylic acid.

Accordingly, the present invention provides a novel process for recovering acrylonitrile from the gross reaction product produced by the fluid-bed ammoxidation of propylene, the gross reaction product being cooled to separate acrylonitrile and HCN therefrom thereby producing an ammoxidation waste gas containing at least 65% nitrogen, propylene and carbon dioxide, the improvement comprising passing the ammoxidation waste gas through a catalytic converter containing a fixed-bed of catalyst capable of converting the propylene in the ammoxidation waste gas to valuable product selected from the group consisting of acrolein, acrylic acid and acrylonitrile to thereby convert the propylene to at least one of the valuable products.

DETAILED DESCRIPTION

The byproduct gas produced by condensing acrylonitrile and HCN from the gross reaction product produced by the fluid-bed catalytic ammoxidation of propylene is the feed processed by the inventive process. Hereinafter, this waste gas will be referred to as "ammoxidation waste gas". Normally, the ammoxidation waste gas will contain roughly 85% $N_2$, 0.1 to 0.5% propylene, 1 to 3% propane with the balance being oxygen, carbon dioxide, carbon monoxide and water. However, the proportion of ingredients in the ammoxidation waste gas may vary outside these ranges if the ammoxidation reactor is operated under conditions other than those which foster maximum production of acrylonitrile in a single pass through the reactor. In any event, the amount of propylene in the waste gas will almost always be between 0.05 and 5%, more typically between 0.1 and 3%. Also, the oxygen content of this gas will usually be no more than 5% and usually between about 0.5 and 3%. Also, the nitrogen content will practically always be at least about 65%, more normally at least about 80%, usually about 85%. Any such ammoxidation waste gas can be processed by the inventive process.

In accordance with the present invention, the ammoxidation waste gas is passed through a catalytic converter containing a catalyst capable of reacting the propylene to produce a valuable product such as acrolein and acrylic acid or alternatively acrylonitrile. As well known, a mixture of propylene and oxygen (air) when contacted with a suitable catalyst will form a mixture of acrolein and acrylic acid. If ammonia is included in the reaction mixture, acrylonitrile is the major product. In accordance with the invention, these oxidation or ammoxidation processes are carried out in a fixed-bed catalytic converter using the propylene in the ammoxidation waste gas effluent as the hydrocarbon reactant.

In this connection, it has already been proposed to carry out the known propylene oxidation and ammoxidation reactions in fixed-bed mode. However, since these reactions are highly exothermic in nature, it is necessary when operating in this way to use a reactor able to remove the great amounts of heat generated by the reaction. In actual practice, shell and tube type reactors are usually employed with the catalyst being housed in many small diameter tubes (tube side) and a heat exchange medium such as water being circulated on the shell side for cooling. Such reactors are expensive and difficult to fill with new catalyst charges. In accordance with the invention, these disadvantages are eliminated or largely ameliorated because the feed gas itself is able to supply all or substantially all of the cooling necessary to keep the reaction temperature within suitable limits. Thus, the catalytic converter employed in the inventive process is different from a conventional fixed-bed reactor used to carry out the known propylene oxidation or ammoxidation reactions in that the cooling capacity of the catalytic converter need only be much less than (e.g. 20% of) the cooling capacity of a conventional reactor. Moreover, in many instances and in accordance with the preferred embodiment of the invention, the amount of propylene in the feed will be so small that no additional cooling is needed. This is particularly advantageous because the catalytic converter in this instance need only be a simple container and is thus inexpensive to build and use.

Catalysts useful in the catalytic converter are conventional. Thus, the catalysts described, for example, in U.S. Pat. Nos. 3,642,930 and 3,766,092, the disclosure of which is incorporated herein by reference, can be employed. Other well known oxidation and ammoxidation catalysts such as those described in commonly assigned patents U.S. Pat. Nos. 3,338,952 and 3,431,292 can be employed. Any catalyst which is capable of catalyzing the reaction of propylene together with oxygen and optionally ammonia to produce acrolein, acrylic acid and/or acrylonitrile can be employed in the catalytic converter of the invention. Hereinafter, these catalysts will be referred to as "converter catalysts".

Other aspects of the converter catalyst are conventional. Thus, the converter catalyst should be particulate in form and have a particle size of 1/32 to ½ inch, preferably 1/16 to ¼ inch, as is conventional. Also, the catalyst may be supported on conventional supports such as silica, alumina, silica/alumina (Alundum), zirconia, titania and so forth.

The amount of oxygen and optionally ammonia to be fed to the catalytic converter of the invention should normally be sufficient to enable complete reaction of the propylene in the ammoxidation waste gas to the desired valuable products. These amounts are well known in the art, and the conventional amounts of oxygen and ammonia are employed in the inventive process. Normally, a slight excess of ammonia (1.05 to 1.3 moles ammonia per mole of propylene) and a slight excess of oxygen (9 to 15 moles air per mole of propylene) are used. Usually the ammoxidation waste gas will not contain these amounts of oxygen and propylene, and accordingly, additional amounts of these reactants will be fed to the catalytic converter.

Other reaction conditions such as temperature, contact time, throughput, etc. are all conventional.

The gaseous reaction product passing out the of the catalytic converter can be processed in a conventional manner to recover acrylonitrile, acrolein and/or acrylic acid. In a preferred embodiment, acrylonitrile and HCN are separated from the catalytic converter product and combined with the acrylonitrile and HCN streams derived from the fluid-bed ammoxidation reactor gross reaction product for processing in the main acrylonitrile recovery and purification train.

The following working examples are provided to more thoroughly illustrate the present invention.

EXAMPLE 1

A gas mixture simulating ammoxidation waste gas and comprising 0.9% propylene, 1.8% $O_2$, 1.8% CO, 3.9 $CO_2$ and 91.5% $N_2$ was contacted with 10 to 30 mesh catalyst comprising 82.5% $K_{0.1}Ni_{2.5}CO_{4.5}Fe_3Bi_1P_0Mo_{12}O_x$ + 17.5% in $SiO_2$ in a 40 cc. fixed-bed reactor at 370° C., atmospheric pressure at a contact time of 2.5 seconds. The effluent gas was analyzed and found to contain 0.0% propylene, 1.8% CO, 4.5 $CO_2$, 0.0% $O_2$ and 92.9% $N_2$. All of the propylene had been reacted with a majority of the propylene being converted to acrolein and acrylic acid, the acrolein yield being 40% based on the propylene fed and the acrylic acid yield being 17% based on the propylene fed.

EXAMPLE 2

Example 1 was repeated except that the feed included a slight stoichiometric excess of ammonia, the reaction temperature was 422° C. and the contact time was 3.5 seconds. The effluent gas contained 0.0% propylene, 1.6% CO, 4.1% $CO_2$, 0.0% $O_2$ and 94.3% $N_2$. The converted propylene could be accounted for as approximately 40% acrylonitrile, 15% HCN and 10% acrolein.

EXAMPLE 3

A mixture of 1 propylene/10.2 air/1.05 ammonia was contacted with a fluid-bed catalyst comprising 50% $K_{0.1}Ni_{2.5}CO_{4.5}Fe_3Bi_1P_{0.5}Mo_{12}O_x$ + 50% $SiO_2$ in a fluid-bed reactor at a contact time of 9.3 seconds at 810° F. The gross reaction product was passed through a water scrubber to yield an ammoxidation waste gas comprising 0.92% propylene, 1.3% CO, 3.52% $CO_2$, 1.4% $O_2$ and 91.9% $N_2$. This ammoxidation waste gas was then contacted with a catalyst comprising 82.5% $K_{0.1}Ni_{2.5}CO_{4.5}Fe_3Bi_1P_{0.5}Mo_{12}O_x$ + 17.5% $SiO_2$ in a 40 cc. fixed-bed reactor at a contact time of 2.5 seconds and a temperature of 435° F. A tail gas analysis was made on the converter reactor effluent, the tail gas analysis showing 0.3% $O_2$, 1.79% CO, 3.65% $CO_2$, 93.4% $N_2$ and 0.0% propylene. This shows that all of the propylene was reacted.

Although only a few embodiments of the invention have been described above, many modifications can be made without departing from the spirit and scope of the invention. For example, the inventive process can be employed on the gross reaction product produced by the fluid-bed ammoxidation of isobutylene to produce methacrylonitrile. All such modifications are intended to be included within the scope of the present invention, which is to be limited only by the following claims.

We claim:

1. In a process for recovering acrylonitrile from the gross reaction product produced by the fluid-bed ammoxidation of propylene, said gross reaction product being cooled to separate acrylonitrile and HCN therefrom thereby producing an ammoxidation waste gas containing at least 65% nitrogen, propylene and carbon dioxide, the improvement comprising passing said ammoxidation waste gas through a catalytic converter containing a fixed-bed of catalyst capable of converting the propylene in said ammoxidation waste gas to valuable product selected from the group consisting of acrolein, acrylic acid and acrylonitrile to thereby convert said propylene to at least one of said valuable products.

2. The process of claim 1 wherein oxygen is fed to said catalytic converter whereby acrolein and acrylic acid are produced.

3. The process of claim 2 wherein air is fed to said catalytic converter.

4. The process of claim 1 wherein oxygen and ammonia are fed to said catalytic converter whereby acrylonitrile is produced.

5. The process of claim 4 wherein air is fed to said catalytic reactor.

* * * * *